United States Patent
Kim et al.

(10) Patent No.: US 10,912,809 B2
(45) Date of Patent: Feb. 9, 2021

(54) ENHANCER FOR CATECHIN UPTAKE IN ENTEROCYTES

(71) Applicant: AMOREPACIFIC CORPORATION, Seoul (KR)

(72) Inventors: Su Kyung Kim, Yongin-si (KR); Jin Oh Chung, Yongin-si (KR); Wan Gi Kim, Yongin-si (KR); Jeong Kee Kim, Yongin-si (KR); Song Seok Shin, Yongin-si (KR); Soon Mi Shim, Seoul (KR); Da Yeon Lee, Seoul (KR); Sang Ryun Yim, Seoul (KR); Eun Hye Choi, Seoul (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 16/471,096

(22) PCT Filed: Nov. 21, 2017

(86) PCT No.: PCT/KR2017/013261
§ 371 (c)(1),
(2) Date: Jun. 19, 2019

(87) PCT Pub. No.: WO2018/124480
PCT Pub. Date: Jul. 5, 2018

(65) Prior Publication Data
US 2020/0016224 A1    Jan. 16, 2020

(30) Foreign Application Priority Data

Dec. 28, 2016 (KR) .................. 10-2016-0181060

(51) Int. Cl.
| | | |
|---|---|---|
| *A61K 36/00* | (2006.01) | |
| *A61K 36/82* | (2006.01) | |
| *A23L 33/105* | (2016.01) | |
| *A61K 31/353* | (2006.01) | |
| *A61K 36/25* | (2006.01) | |
| *A61K 36/8962* | (2006.01) | |

(52) U.S. Cl.
CPC ............ *A61K 36/82* (2013.01); *A23L 33/105* (2016.08); *A61K 31/353* (2013.01); *A61K 36/25* (2013.01); *A61K 36/8962* (2013.01)

(58) Field of Classification Search
None
See application file for complete search history.

(56) References Cited

U.S. PATENT DOCUMENTS

| | | |
|---|---|---|
| 9,358,310 B2 | 6/2016 | Katti et al. |
| 2009/0047408 A1 | 2/2009 | Unno et al. |
| 2012/0177738 A1 | 7/2012 | Lambelet et al. |
| 2015/0283251 A1 | 10/2015 | Hwang et al. |
| 2015/0313999 A1 | 11/2015 | Actis Goretta et al. |

FOREIGN PATENT DOCUMENTS

| | | | |
|---|---|---|---|
| JP | 2010-011751 A | | 1/2010 |
| JP | 4807563 B2 | | 11/2011 |
| JP | 2012-528125 A | | 11/2012 |
| JP | 2016-504020 A | | 2/2016 |
| JP | 2016-093143 A | | 5/2016 |
| JP | 2016-216440 A | | 12/2016 |
| KR | 10-2004-0077035 A | | 9/2004 |
| KR | 10-2007-0032458 A | | 3/2007 |
| KR | 10-2014-0072307 A | | 6/2014 |
| KR | 10-1423433 B1 | | 8/2014 |
| KR | 10-2015-0031557 A | | 3/2015 |
| KR | 2015031557 A | * | 3/2015 |
| KR | 10-2015-0138068 A | | 12/2015 |
| KR | 1591708 B1 | * | 2/2016 |
| KR | 10-2016-0046446 A | | 4/2016 |

OTHER PUBLICATIONS

Eun-Hye Choi et al., "Influence of flavonol-rich excipient food (onion peel and Dendropanax morbifera) on the bioavailability of green tea epicatechins in vitro and in vivo", Food & Function, 2017, pp. 3664-3674, vol. 8.
International Search Report of PCT/KR2017/013261 dated Dec. 10, 2018 [PCT/ISA/210].

* cited by examiner

*Primary Examiner* — Qiuwen Mi
(74) *Attorney, Agent, or Firm* — Sughrue Mion, PLLC

(57) ABSTRACT

The present invention relates to an enhancer for catechin uptake enhancer in enterocytes, wherein, by mixing a green tea extract containing catechin as an active ingredient, a *Dendropanax morbifera* extract, and an onion extract at a proper ratio, the stability in the digestive organ can be improved and, eventually, the catechin uptake in enterocytes can be enhanced.

6 Claims, 2 Drawing Sheets

[Figure 1]
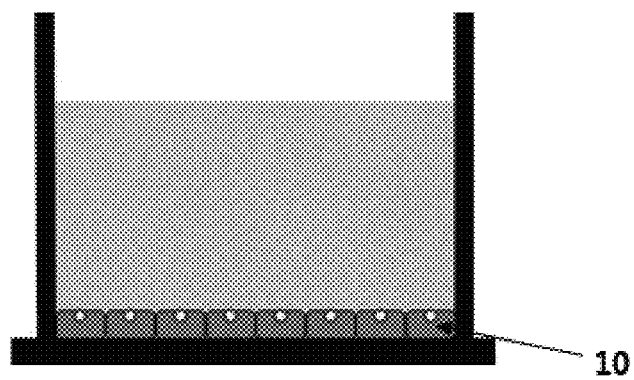
[Figure 2A]
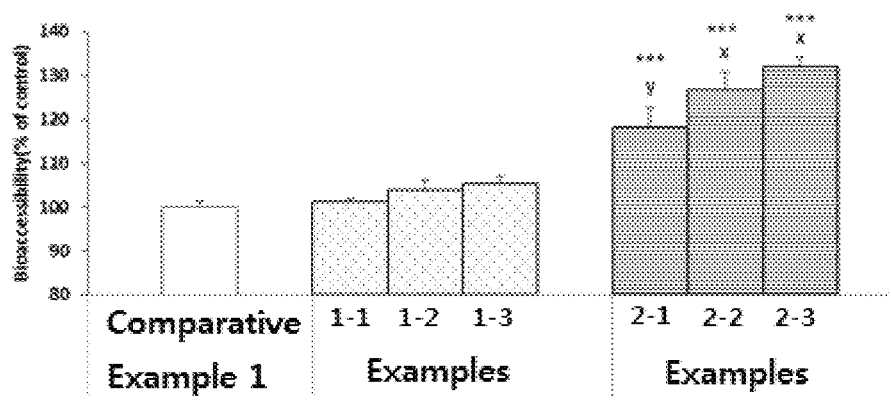

【Figure 2B】
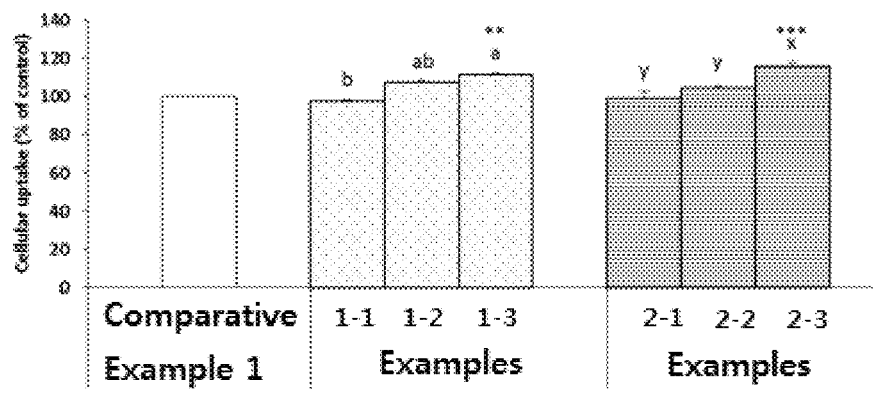
【Figure 3】
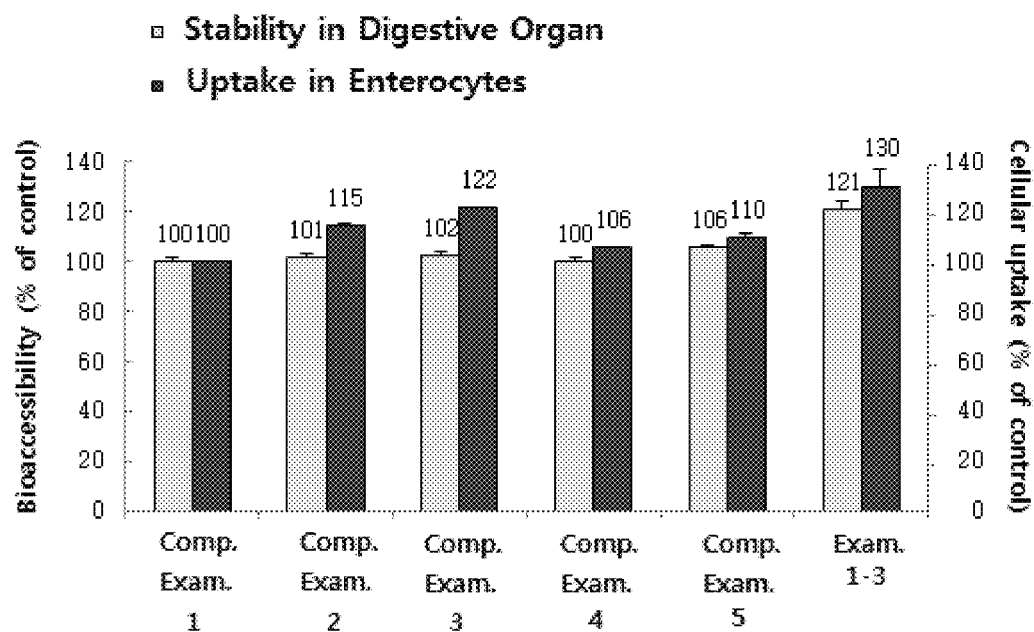

ENHANCER FOR CATECHIN UPTAKE IN ENTEROCYTES

CROSS REFERENCE TO RELATED APPLICATIONS

This application is a National Stage of International Application No. PCT/KR2017/013261, filed Nov. 21, 2017, claiming priority to Korean Patent Application No. 10-2016-0181060, filed Dec. 28, 2016, the contents of all of which are incorporated herein by reference in their entirety.

TECHNICAL FIELD

The present invention relates to an enhancer for catechin uptake in enterocytes, and more particularly, to an enhancer for catechin uptake in enterocytes using a green tea extract containing catechin as an active ingredient.

BACKGROUND ART

A green tea extract has been known to have a variety of biological activities due to the presence of catechin serving as an active ingredient. However, the green tea extract has a drawback in that it is easily deformed under physical conditions such as pH, oxygen concentration, and chemical conditions as in rapid in vivo enzymatic metabolisms, resulting in degraded bioavailability in the body.

In general, catechin has been known to be absorbed at a level of intake of less than 2% in the guts. In this case, such catechin is considered to have the low bioavailability because catechin is sensitive to the conditions of digestive fluids in the body, has a low uptake in enterocytes, and rapidly metabolizes and secretes in the small intestine. For these reasons, the catechin is mainly decomposed during a digestive process in an upper portion of the small intestine which has a high pH level and in which active oxygen exists. In this case, antiporters such as P-glycoproteins reversely transport catechin into the guts without penetrating through the enterocytes.

In recent years, it has been known that, when glycocomponents such as sugar are added to the tea extract containing catechin, the stability of catechin in the digestive organ is improved and the accumulation rate of catechin in enterocytes is enhanced, indicating that the uptake of catechin in the body may be enhanced due to the addition of the glycocomponents. However, the glycocomponents such as sugar have a problem in that they are low-nutrition and high-calorie components that may have a negative effect on the health of some users. Therefore, there is a need for an alternative method capable of enhancing the uptake of catechin in enterocytes.

Accordingly, there is a need for development of technology capable of ensuring physical and metabolic stabilization of catechin contained in the green tea extract when present in the body, thereby enhancing the uptake of catechin in the enterocytes.

Prior-Art Document

Patent Documents

Patent Document 1: Japanese Patent Laid-Open Publication No. 2010-011751 entitled "Enhancer for Absorption of Phenolic Compounds and Use Thereof"

Patent Document 2: Korean Patent Application Publication No. 2007-0032458 entitled "*Dendropanax morbifera* Tea and Manufacturing Method Thereof"

DISCLOSURE

Technical Problem

The present inventors have conducted lots of research to solve the above problems and found that, when a *Dendropanax morbifera* extract and an onion extract are mixed at proper amounts with a green tea extract containing catechin as an active ingredient, the in vivo stability of catechin in the digestive organ can be ensured, thereby enhancing the uptake of catechin in enterocytes.

Therefore, an object of the present invention is to provide an enhancer for catechin uptake in enterocytes.

Another object of the present invention is to provide an antioxidant health food composition including the enhancer for catechin uptake in the enterocytes.

Still another object of the present invention is to provide an antioxidant pharmaceutical composition including the enhancer for catechin uptake in the enterocytes.

Technical Solution

To solve the above problems, according to one aspect of the present invention, there is provided an enhancer for catechin uptake in enterocytes, which includes a green tea extract containing catechin as an active ingredient; a *Dendropanax morbifera* extract; and an onion extract.

A mixture of the *Dendropanax morbifera* extract and the onion extract may be included at a content of 1 to 4 parts by weight, preferably 2 to 4 parts by weight, based on 100 parts by weight of the green tea extract containing catechin as the active ingredient.

In this case, a weight ratio of the *Dendropanax morbifera* extract and the onion extract may be in a range of 1:1 to 1:4.

The green tea extract, the *Dendropanax morbifera* extract and the onion extract may be a green tea leaf extract, a *Dendropanax morbifera* leaf extract and an onion skin extract, respectively.

According to another aspect of the present invention, there is provided an antioxidant health food composition including the enhancer for catechin uptake in enterocytes.

The antioxidant health food composition may be formulated into one or more selected from the group consisting of tablets, liquids, capsules, pills, granules, drinks, caramels, diet bars, jellies, oral films, and tea bags.

Still according to another aspect of the present invention, there is provided an antioxidant pharmaceutical composition including the enhancer for catechin uptake in enterocytes.

Advantageous Effects

The enhancer for catechin uptake in enterocytes according to the present invention can ensure the stability of catechin in the digestive organ, thereby enhancing the uptake of catechin in the enterocytes.

Therefore, the enhancer for catechin uptake in enterocytes can be widely used for antioxidant foods and drugs requiring the high bioavailability of catechin.

DESCRIPTION OF DRAWINGS

FIG. 1 is a conceptual diagram of a small intestine model according to Experimental Example 1 of the present invention.

FIG. 2A is a graph illustrating the stabilities in the digestive organ of enhancers for catechin uptake according to Examples 1 and 2 and Comparative Example 1 of the present invention.

FIG. 2B is a graph illustrating the uptakes in enterocytes of the enhancers for catechin uptake according to Examples 1 and 2 and Comparative Example 1 of the present invention.

FIG. 3 is a graph illustrating the stabilities in the digestive organ and the uptakes in the enterocytes of the enhancers for catechin uptake according to Comparative Examples 1 to 5 and Examples 1-3 of the present invention.

BEST MODE

Hereinafter, the present invention will be described in further detail in order to aid in understanding the present invention.

The terms and words used in this specification and the claims are not intended to be construed as having common and dictionary meanings but are construed as having meanings and concepts corresponding to the technical spirit of the present invention in view of the principle that the present inventors can properly define the concepts of the terms and words in order to describe his/her invention with the best method.

The present invention relates to an enhancer for catechin uptake in enterocytes which is capable of enhancing the uptake of catechin in enterocytes, which is contained in a green tea extract, to improve the bioavailability of catechin.

The enhancer for catechin uptake according to the present invention may include a green tea extract containing catechin as an active ingredient; a *Dendropanax morbifera* extract; and an onion extract.

Catechin is a kind of polyphenols that is used as a meaning of generally referring to catechins, and types of such catechins include (+)-catechin (C), (−)-epicatechin (EC), (−)-gallocatechin (GC), (−)-epigallocatechin (EGC), (−)-catechin gallate (CG), (−)-epicatechin gallate (ECG), (−)-gallocatechin gallate (GCG), and (−)-epigallocatechin gallate (EGCG). In the present invention, "catechin" is used as a meaning of referring to part or all of the catechins listed above.

As the active ingredient, the catechin may be contained at a content of 20% by weight or more, preferably 30 to 50% by weight, based on the total weight of the green tea extract.

The green tea extract may be an extract of one or more selected from the group consisting of leaves, stems and roots.

In the present invention, the *Dendropanax morbifera* extract and the onion extract may enhance the stability of catechin, which is contained as the active ingredient in the green tea extract, in the digestive organ and the uptake of catechin in the enterocytes.

The enhancer for catechin uptake in enterocytes according to the present invention may include 1 to 4 parts by weight, preferably 2 to 4 parts by weight, of a mixture of the *Dendropanax morbifera* extract and the onion extract, based on 100 parts by weight of the green tea extract containing catechin as the active ingredient.

When the content of the mixture is less than 1 part by weight, the stability of catechin in the digestive organ and the uptake of catechin in the enterocytes may be reduced. On the other hand, when the content of the mixture is greater than 4 parts by weight, the content of catechin in the enhancer may be relatively reduced, resulting in a degraded effect on biological activities of catechin.

Also, when the content of the mixture is in a range of 2 to 4 parts by weight, the stability of catechin in the digestive organ and the uptake of catechin in the enterocytes may be further improved.

The *Dendropanax morbifera* extract may be an extract of one or more selected from the group consisting of leaves, stems and roots of *Dendropanax morbiferus*, and the *Dendropanax morbifera* extract may be an undiluted extract of 100% *Dendropanax morbiferus*.

The onion extract may be an extract of one or more selected from the group consisting of cataphylls, skins and roots of *Allium cepa*.

In the present invention, the *Dendropanax morbifera* leaf extract and the onion skin extract may be used in consideration of effects of stabilizing catechin in the digestive organ and enhancing the uptake of catechin in enterocytes.

Meanwhile, the weight ratio of the *Dendropanax morbifera* extract and the onion extract mixed in the mixture may be in a range of 1:1 to 1:4. In this case, when the weight ratio falls out of this weight ratio range, the effects of stabilizing catechin in the digestive organ and enhancing the uptake of catechin in enterocytes may be deteriorated. Also, when the weight ratio falls within this weight ratio range, the effects of stabilizing catechin in the digestive organ and enhancing the uptake of catechin in enterocytes may be improved with an increasing content of the onion extract.

The green tea extract, the *Dendropanax morbifera* extract and the onion extract used in the present invention may be prepared by methods known in the related art. In this case, the methods are not particularly limited. Specifically, the extracts may be prepared using water or an organic solvent. The organic solvent used in the present invention may be selected from the group consisting of ethanol, methanol, butanol, ether, ethyl acetate, chloroform, and a mixed solvent of these organic solvents and water. Preferably, 80% ethanol may be used. In this case, the extraction temperature is preferably in a range of 10 to 80° C., and the extraction may be performed for 3 to 24 hours. When the extraction temperature and the extraction time fall out of these ranges, the extraction efficiency may be deteriorated, or the components may be degenerated.

Also, the present invention relates to an antioxidant health food composition including the enhancer for catechin uptake in enterocytes as described above. In this case, an antioxidant effect may be improved due to the improved uptake of catechin, thereby preventing or ameliorating aging.

The health food composition may be a health food, a functional food, and a food additive composition. The health food composition is applicable to various formulations such as tablets, liquids, capsules, pills, granules, drinks, caramels, diet bars, jellies, oral films, and tea bags using a conventional method which includes adding various types of excipients or additives. In addition to the active ingredient, a person having ordinary skill in the art may properly select and blend components generally used in the related art without any difficulty, depending on the formulations and purposes of use. In this case, such components may have a synergy effect when bended with other components.

Also, the present invention relates to an antioxidant pharmaceutical composition including the enhancer for catechin uptake in enterocytes as described above. In this case, an antioxidant effect may be improved due to the improved uptake of catechin, thereby preventing or healing (i.e., inhibiting) aging.

The pharmaceutical composition according to the present invention may be orally administered in the form of a solid, semisolid or liquid phase after a commercially available inorganic or organic carrier is added thereto. A preparation for oral administration may include tablets, soft and hard capsules, pills, granules, powders, grains, solutions, emulsions, syrups, pellets, oral films, and the like.

The pharmaceutical composition may be readily formulated according to methods generally known in the art. In this case, a surfactant, an excipient, a pigmenting agent, a seasoning agent, a preservative, a stabilizing agent, a buffering agent, a suspending agent, or other commercially available adjuvants may be used in suitable amounts.

Also, the dose of the active component may vary depending on the age, sex, and weight of a subject to be treated, and a disease and pathological conditions to be treated, a route of administration, or the prescriber's judgment. The dosage determined based on these factors falls within a range determined by those skilled in the art. For example, the pharmaceutical composition may be administered once or three times a day at 100 to 1,000 mg, preferably 300 to 600 mg. In this case, the dose of the pharmaceutical composition is not intended to limit the scope of the present invention by means of any methods.

The pharmaceutical composition may be administered as an individual therapeutic agent or administered in combination with other therapeutic agents, and may be administered sequentially or concomitantly with conventional therapeutic agents. It is important to administer the pharmaceutical composition at an amount that can exhibit the maximum effect when used in a minimal amount without causing any side effects in consideration of all the aforementioned factors. In this case, the amount of the pharmaceutical composition may be readily determined by those skilled in the art.

In addition to the aforementioned components, the antioxidant health food composition or the antioxidant pharmaceutical composition according to the present invention may further include other components capable of enhancing the bioavailability of catechin at levels of contents that do not inhibit the efficiency of catechin. For example, the composition may include one or more selected from sugars, acids, sugar alcohols, and the like.

MODE FOR INVENTION

Hereinafter, the present invention will be described in further detail with reference to Examples thereof. However, it should be understood that the following examples are not intended to limit the scope of the present invention, but are intended to aid in understanding the present invention.

Preparation Example 1: Preparation of Green Tea Leaf Extract Containing Catechin as Active Ingredient Green tea leaves primarily processed in a roasting process and 70% ethanol were added to an extraction bath, and the resulting mixture was extracted at 60° C. for 3 hours. A liquid fraction was separated from the extract, filtered, and then stirred while adding acid clay thereto. Thereafter, the resulting mixture was filtered through a filter paper, concentrated, and spray-dried to prepare a green tea leaf extract in a powdery phase. The content of catechin included in the prepared green tea leaf extract was 35% by weight, based on the total weight of the extract.

Preparation Example 2: Preparation of *Dendropanax Morbifera* Extract

Dried *Dendropanax morbifera* leaves were primarily extracted using fermentation alcohol, and then filtered to give a primary extract. The primary extract was secondarily extracted using purified water, filtered, and then concentrated to give a secondary extract. The secondary extract was sterilized and dried to prepare a *Dendropanax morbifera* leaf extract in a powdery phase.

Preparation Example 3: Preparation of Onion Extract

Ground onion was extracted using fermentation alcohol, filtered, concentrated, purified on columns, and then dried to prepare an onion extract in a powdery phase.

Examples 1 and 2: Preparation of Enhancers for Catechin Uptake

Based on the compositions as listed in the following Table 1, the green tea leaf extract, the *Dendropanax morbifera* leaf extract and the onion extract prepared in Preparation Examples 1 to 3, respectively, were mixed to prepare enhancers for catechin uptake.

Comparative Example 1:Green Tea Leaf Extract

The green tea leaf extract prepared in Preparation Example 1, which contained catechin as the active ingredient, was prepared as the control.

Comparative Examples 2 and 3:Preparation of Enhancers Using Green Tea Leaf Extract and *Dendropanax Morbifera* Leaf Extract Based on the compositions as listed in the following Table 2, the green tea leaf extract and the *Dendropanax morbifera* leaf extract prepared in Preparation Examples 1 and 2, respectively, were mixed to prepare enhancers for catechin uptake.

Comparative Examples 4 and 5: Preparation of Enhancers Using Green Tea Leaf Extract and Onion Extract Based on the compositions as listed in the following Table 3, the green tea leaf extract and the onion extract prepared in Preparation Examples 1 and 3, respectively, were mixed to prepare enhancers for catechin uptake.

TABLE 1

| | | Enhancer for catechin uptake (parts by weight) | | |
|---|---|---|---|---|
| | | Green tea leaf extract | Mixture of *Dendropanax morbifera* leaf extract and onion extract | Weight ratio of mixture *Dendropanax morbifera* leaf extract:onion extract |
| Example 1 | 1-1 | 100 | 2 | 1:1 |
| | 1-2 | 100 | 2 | 1:2 |
| | 1-3 | 100 | 2 | 1:4 |
| Example 2 | 2-1 | 100 | 4 | 1:1 |
| | 2-2 | 100 | 4 | 1:2 |
| | 2-3 | 100 | 4 | 1:4 |

TABLE 2

| | Green tea leaf extract (parts by weight) | Dendropanax morbifera leaf extract (parts by weight) | Onion extract (parts by weight) |
|---|---|---|---|
| Comparative Example 1 | 100 | — | — |
| Comparative Example 2 | 100 | 2 | — |
| Comparative Example 3 | 100 | 5 | — |
| Comparative Example 4 | 100 | — | 2 |
| Comparative Example 5 | 100 | — | 5 |

Experimental Example 1: Evaluation of Stability in Digestive Organ

Each of the enhancers prepared in Examples and Comparative Examples was continuously incubated for 3 hours in an artificial digestive fluid as an in vitro model of biodigestion evaluation. Thereafter, the stabilities of four catechins in the digestive organ were evaluated by taking the digested products after a small intestine phase, and analyzing the contents of the catechins using an UPLC-PDA-ESI-MS/MSn system. The analysis conditions for the UPLC-PDA-ESI-MS/MSn system are as listed in the following Table 3. In this case, the catechin includes four types of epicatechin (EC), epigallocatechin (EGC), epicatechin gallate (ECG), and epigallocatechin gallate (EGCG).

Specifically, each of the enhancers prepared in Examples and Comparative Examples was dissolved in 6 mL of a phosphate buffer, 4 mL of amylase was added thereto, and the resulting mixture was then incubated at 37° C. for 3 minutes. Thereafter, 8 mL of a pepsin solution was added, and the mixture was adjusted to pH 2 using hydrochloric acid, and then incubated at 37° C. for an hour. For the conditions of a pre-small intestine phase, sodium hydrogen carbonate ($NaHCO_3$) was added, and the mixture was adjusted to pH 3. And, 4 mL of each of bile acid, lipase, pancreatin solutions serving as digestive enzymes in the small intestine, and the mixture was adjusted to pH 7 using a sodium hydroxide (NaOH) solution. The mixture was incubated again at 37° C. for 2 hours, and centrifuged to obtain a supernatant only. Then, the contents of the four catechins were analyzed using the UPLC-PDA-ESI-MS/MSn system, and the digestive stability (bioaccessibility, % of control) was then evaluated.

TABLE 3

| | Analysis conditions for UPLC-PDA-ESI-MS/MSn system |
|---|---|
| Auto sampler | Accela Autosampler |
| Mobile phase | 0.1% Acetic acid, Acetonitrile |
| Detector | UV 280 nm |
| Injection volume | 20 µL |
| Column temp. | 40° C. |
| Flow rate | 1 mL/min |
| Column | C18 (250 * 4.6 MM, Pore size: 5 µm) |

Experimental Example 2: Evaluation of Uptake in Enterocytes

To check the uptake of catechin in enterocytes for each of the enhancers prepared in Examples and Comparative Examples, enterocytes (Caco-2) were selected, and tested using a 6-well-sized mono plate (Cat. 140675, sterile, Nunclon).

FIG. 1 is a conceptual diagram of a small intestine model according to Experimental Example 1 of the present invention.

As shown in FIG. 1, Caco-2 cells (10) were seeded in a mono plate at a density of $3 \times 10^5$ cells/well, and then incubated for 2 weeks under conditions of 5% $CO_2$ and 37° C. until the Caco-2 cells grew to 100% confluence in order to create an environment similar to the small intestine of the human body. The Caco-2 cells were washed with phosphate-buffered saline (PBS) at intervals of 3 to 5 days, and a Dulbeco's Modified Eagle's medium (DMEM) was replaced.

To treat enterocytes with the enhancer which had undergone the in vitro biodigestion evaluation, first of all, the enhancer was washed with PBS for 30 minutes, and seeded. The enhancer was incubated for 2 hours under conditions of 5% $CO_2$ and 37° C., and only the cells were separated, and then pulverized with a protease to analyze the uptake of the enhancer in the enterocytes using the UPLC-PDA-ESI-MS/MSn system. The analysis conditions for the UPLC-PDA-ESI-MS/MSn system are as listed in the Table 3.

FIGS. 2A and 2B are graphs illustrating the stabilities in the digestive organ and the uptakes in the enterocytes of the enhancers for catechin uptake according to Examples 1 and 2 and Comparative Example 1 of the present invention.

Referring to FIGS. 2A and 2B, it can be seen that all the enhancers for catechin uptake according to Examples 1-1 to 1-3 and Examples 2-1 to 2-3 showed the excellent stabilities (A) in the digestive organ and the high uptakes (B) in the enterocytes.

FIG. 3 is a graph illustrating the stabilities in the digestive organ and the uptakes in the enterocytes of the enhancers for catechin uptake according to Comparative Examples (Comp. Exam.) 1 to 5 and Examples (Exam.) 1-3 of the present invention.

Referring to FIG. 3, it can be seen that all the enhancers for catechin uptake of Example 1-3 including the green tea leaf extract, the *Dendropanax morbifera* leaf extract and the onion extract at proper contents showed the superior stabilities in the digestive organ and the high uptakes in the enterocytes, compared to those of Comparative Examples 1 to 5.

Formulation examples of the enhancer for catechin uptake according to one aspect of the present invention will be described below. However, it should be understood that the enhancer for catechin uptake may be applied to various other formulations, the contents of which are intended to describe the present invention in detail, but not intended to limit the scope of the present invention.

[Formulation Example 1]Tablets

60% by weight of a green tea extract, 2% by weight of an enhancer for catechin uptake, 2% by weight of ascorbic acid, and 34.1% by weight of crystalline cellulose, 1.0% by weight of silicon dioxide, and 0.9% by weight of magnesium stearate are tableted by conventional methods to prepare tablets.

[Formulation Example 2]Pills

28% by weight of a green tea extract, 2% by weight of an enhancer for catechin uptake, 10% by weight of citric acid, 10% by weight of xylitol, 10% by weight of corn starch, 20% by weight of glycerin, and 20% by weight of sorbitol are mixed, and the resulting mixture is prepared into pills using a pill-making machine.

[Formulation Example 3] Granules

18% by weight of a green tea extract, 2% by weight of an enhancer for catechin uptake, 10% by weight of ascorbic acid, 10% by weight of xylitol, 5% by weight of enzymatically modified stevia, and 55% by weight of isomalt are mixed, and then shaped into granules using a fluidized bed granulator. Thereafter, the granules are packed into bags.

[Formulation Example 4] Health Drinks

10% by weight of a green tea extract, 1% by weight of an enhancer for catechin uptake, 10% by weight of enzymatically modified stevia, 10% by weight of a grapefruit concentrate, and the balance of purified water are mixed, and the resulting mixture is then heated at 85° C. for an hour while stirring according to a conventional method of preparing a health drink. Thereafter, the resulting solution is filtered, and packed into a sterile vessel, which is hermetically sealed, sterilized, and kept refrigerated. This solution is used for preparation of health drink compositions.

INDUSTRIAL APPLICABILITY

The enhancer for catechin uptake in enterocytes according to the present invention can be widely used for antioxidant foods and drugs requiring the high bioavailability of catechin.

The invention claimed is:

1. A method for enhancing catechin uptake in enterocytes of a subject, comprising administering a composition comprising a green tea extract containing catechin as an active ingredient; a *Dendropanax morbifera* extract; and an onion extract, to the subject,
   wherein the composition comprises 1 to 4 parts by weight of a mixture of the *Dendropanax morbifera* extract and the onion extract, based on 100 parts by weight of the green tea extract containing the catechin as the active ingredient.

2. The method of claim 1, wherein the composition comprises 2 to 4 parts by weight of the mixture of the *Dendropanax morbifera* leaf extract and the onion extract, based on 100 parts by weight of the green tea extract containing the catechin as the active ingredient.

3. The method of claim 1, wherein a weight ratio of the *Dendropanax morbifera* extract and the onion extract is in a range of 1:1 to 1:4.

4. The method of claim 1, wherein the green tea extract, the *Dendropanax morbifera* extract and the onion extract are a green tea leaf extract, a *Dendropanax morbifera* leaf extract and a whole onion bulb extract, respectively.

5. The method of claim 1, wherein the composition is a dietary supplement or foodstuff in a formulation selected from the group consisting of a tablet, liquid, a capsule, a pill, a granule, a drink, a caramel, a diet bar, a jelly, an oral film, and a tea bag.

6. The method of claim 1, wherein the composition is a pharmaceutical composition which further comprises a pharmaceutically acceptable carrier.

* * * * *